(12) United States Patent
Mizukami et al.

(10) Patent No.: US 7,405,082 B2
(45) Date of Patent: Jul. 29, 2008

(54) METHODS AND DEVICES FOR MEASURING RETICULOCYTES

(75) Inventors: Toshihiro Mizukami, Kobe (JP);
Yusuke Mori, Kobe (JP); Kanako Horisaka, Akashi (JP); Sunao Atogami, Nagasaki (JP)

(73) Assignee: Sysmex Corporation, Kobe-shi (JP)

( * ) Notice: Subject to any disclaimer, the term of this patent is extended or adjusted under 35 U.S.C. 154(b) by 773 days.

(21) Appl. No.: 10/655,739

(22) Filed: Sep. 5, 2003

(65) Prior Publication Data

US 2004/0132196 A1 Jul. 8, 2004

(30) Foreign Application Priority Data

Sep. 10, 2002 (JP) ............................. 2002-264478

(51) Int. Cl.
*G01N 33/48* (2006.01)
*G01N 21/64* (2006.01)
(52) U.S. Cl. .................... 436/63; 436/8; 436/10; 436/164; 436/172; 422/73; 422/82.05; 422/82.08; 435/2
(58) Field of Classification Search .......... 436/8, 436/10, 63, 164, 172; 422/73, 82.05, 82.08, 422/82.09; 435/2
See application file for complete search history.

(56) References Cited

U.S. PATENT DOCUMENTS

| 5,006,986 | A | * | 4/1991 | Inoue | 356/39 |
| 5,117,357 | A | * | 5/1992 | Inoue | 356/39 |
| 6,525,807 | B1 | * | 2/2003 | Morikawa et al. | 356/72 |
| 6,670,191 | B2 | * | 12/2003 | Jiang et al. | 436/63 |
| 6,842,233 | B2 | * | 1/2005 | Narisada et al. | 356/39 |
| 6,979,570 | B2 | * | 12/2005 | Narisada | 436/63 |
| 7,049,093 | B2 | * | 5/2006 | Tsuji et al. | 435/39 |

OTHER PUBLICATIONS

Briggs, C.; Rogers, R.; Thompson, B.; Machin, S.J., "New Red Cell Parameters on the Sysmex XE-2100™ as Potential Markers of Functional Iron Deficiency", *Infusion Therapy and Transfusion Medicine*, 2001, vol. 28, pp. 256-262.
Lesesve, J.F.; Lacombe, F.; Marit, G; Bernard, P.; Belloc, F.; Reiffers, J., "High fluorescence reticulocytes are an indicator of bone marrow recovery after chemotherapy", *European Journal of Haematology*, 1995, vol. 54, pp. 61-63.

* cited by examiner

*Primary Examiner*—Maureen M. Wallenhorst
(74) *Attorney, Agent, or Firm*—Brinks Hofer Gilson & Lione (57) ABSTRACT

Methods and devices are described for monitoring a therapeutic effect in a red blood cell-related disease by detecting the size of a reticulocyte using a full-automatic blood cell counting device.

12 Claims, 6 Drawing Sheets

METHODS AND DEVICES FOR MEASURING RETICULOCYTES

FIELD OF THE INVENTION

The present invention relates to methods for monitoring a therapeutic effect in a red blood cell-related disease. More particularly, the present invention relates to methods for monitoring a therapeutic effect in any of various red blood cell-related diseases by detecting the size of a reticulocyte using a full-automatic blood cell counting device.

BACKGROUND

A reticulocyte is the youngest red blood cell that has been denucleated. An increase in reticulocyte serves as an index of the increase in red blood cell production in bone marrow. The inside of a reticulocyte contains RNA that is a residue of a nucleus, which is present as a reticular granule. While it is observed as a large polychromatic red blood cell in an ordinary Wright's staining, it may be stained as a reticule or granule in a supravital staining. It is represented usually as a reticulocyte rate per 1000 red blood cells (0/00; pro Mille).

The reticulocyte count increases or decreases in response to increase or decrease in the production of red blood cells. Since its elevation precedes the red blood cell count or hemoglobin level in the treatment of an iron deficiency anemia or megaloblastic anemia, it is useful in evaluating therapeutic effect at an early stage.

Diseases characterized by an increase in reticulocyte count include, for example, hemolytic anemia, vitamin B12 deficiency anemia, folic acid deficiency anemia, iron deficiency anemia, megaloblastic anemia, and the like. Hemolytic anemia is accompanied by a reduced lifetime of red blood cells, increased serum, indirect reacting bilirubin, reduced haptoglobin, and the like. Diseases exhibiting reduced reticulocyte count should be diagnosed based on bone marrow findings in addition to peripheral blood findings, and include, for example, acute leukemia, aplastic anemia, and the like.

With regard to reticulocyte counting technology, a flow cytometric counting technology has been employed (see, for example: U.S. Pat. Nos. 4,544,546; 4,957,870; 5,360,739; and 5,821.127), and an automatic blood cell counter incorporating this technology has been marketed.

An automatic blood cell counting device may measure the degree of maturity of a reticulocyte in addition to reticulocyte count (rate). The clinical significance of measuring the degree of maturity of a reticulocyte is related to the chemotherapy, hematopoietic recovery monitoring after a bone marrow implantation. When attempts are made to recover bone marrow function that was once suppressed (e.g., by an anticancer agent) by discontinuing chemotherapy, an increase in the count of rather young reticulocytes reportedly precedes others by 2 to 3 days (see, for example: "High fluorescence reticulocytes are an indicator of bone marrow recovery after chemotherapy" in *Eur. J. Haematol.*, 1995, 54, 61-63). Since clinical practitioners expect bone marrow function recovery to be achieved as soon as possible, an identification of the recovery at an early stage is of a great significance.

In the past, the count and the degree of maturity of a reticulocyte were typically the only parameters taken into consideration in diagnosing an anemia or in monitoring the hematopoietic condition after chemotherapy. Heretofore, the size of a newly produced red blood cell (reticulocyte) has not been taken into consideration.

It would be extremely useful in investigating the effect of a therapeutic agent to monitor the size of a reticulocyte. Nevertheless, conventional approaches, which take only the number (rate) or maturity of reticulocytes into consideration, are at risk of producing false judgments as to whether a newly produced red blood cell has a normal function or not.

Moreover, conventional measurements of reticulocytes, when employed alone, pose a problem in that a red blood cell having a low hemoglobin content can not be detected even if it is produced. In erythropoietin therapy for a renal anemia patient in which the production of red blood cells in the bone marrow is increased, a simple deficiency of stored iron is combined with the inability to transport the stored iron to the bone marrow on time (i.e., functional iron deficiency). This is observed clinically when the response to erythropoietin becomes poor in spite of the normal index of kinetics for existing iron species (e.g., iron and ferritin), and leads to the production of a hypochromic red blood cell whose hemoglobin level is reduced.

As described above, the conditions of functional iron deficiency can not be fully assessed if only the number and the rate of a reticulocyte are observed.

SUMMARY

The scope of the present invention is defined solely by the appended claims, and is not affected to any degree by the statements within this summary.

A first method for measuring a reticulocyte embodying features of the present invention includes: (a) preparing a measurement sample by mixing a reticulocyte measurement reagent and a whole blood sample from a subject; (b) introducing the measurement sample into a flow cell of a flow cytometer; (c) irradiating cells in the measurement sample flowing in the flow cell with an excitation light; (d) detecting scattering light and fluorescent light emitted from the cells; (e) making a two-dimensional distribution diagram having two axes corresponding to forward scattering light intensity and fluorescent light intensity, respectively; (f) specifying a mature red blood cell region and a reticulocyte region in the two-dimensional distribution diagram; (g) calculating a first mean forward scattering light intensity in the reticulocyte region; (h) calculating a second mean forward scattering light intensity by performing (a) through (g) using a whole blood sample taken from the subject after a period of time; and (i) detecting a difference between the first and the second mean forward scattering light intensities.

A second method for measuring a reticulocyte embodying features of the present invention includes: (a) preparing a measurement sample by mixing a reticulocyte measurement reagent and a whole blood sample; (b) introducing the measurement sample into a flow cell of a flow cytometer; (c) irradiating cells in the measurement sample flowing in the flow cell with an excitation light; (d) detecting scattering light and fluorescent light emitted from the cells; (e) making a two-dimensional distribution diagram having two axes corresponding to forward scattering light intensity and fluorescent light intensity, respectively; (f) specifying a mature red blood cell region and a reticulocyte region in the two-dimensional distribution diagram; (g) dividing the reticulocyte region into a plurality of regions on the basis of the fluorescent light intensity; and (h) calculating a mean forward scattering light intensity and a mean fluorescent light intensity for each of the plurality of regions.

A third method for measuring a reticulocyte embodying features of the present invention includes: (a) preparing a measurement sample containing a reticulocyte measurement reagent and a first whole blood sample; (b) introducing the measurement sample into a flow cell of a flow cytometer; (c)

irradiating cells in the measurement sample flowing in the flow cell with an excitation light; (d) detecting scattering light and fluorescent light emitted from the cells; (e) making a two-dimensional distribution diagram having two axes corresponding to forward scattering light intensity and fluorescent light intensity, respectively; (f) specifying a mature red blood cell region and a reticulocyte region in the two-dimensional distribution diagram; (g) calculating a mean forward scattering light intensity and a mean fluorescent light intensity in the mature red blood cell region; and (h) calculating a first slope of a first linear regression line representing a relationship between the mean forward scattering light intensity and the mean fluorescent light intensity.

A fourth method for measuring a reticulocyte embodying features of the present invention includes: (a) preparing a measurement sample containing a reticulocyte measurement reagent and a whole blood sample; (b) introducing the measurement sample into a flow cell of a flow cytometer; (c) irradiating cells in the measurement sample flowing in the flow cell with an excitation light; (d) detecting scattering light and fluorescent light emitted from the cells; (e) making a two-dimensional distribution diagram having two axes corresponding to forward scattering light intensity and fluorescent light intensity, respectively; (f) specifying a mature red blood cell region and a reticulocyte region in the two-dimensional distribution diagram; (g) calculating a mean forward scattering light intensity in the mature red blood cell region and a mean forward scattering light intensity in the reticulocyte region; (h) plotting data obtained in (g) on a graph having two axes corresponding to the forward scattering light intensity in the mature red blood cell region and the forward scattering light intensity in the reticulocyte region, respectively; and (i) calculating distance of the data plotted in (h) from a datum point predetermined on the graph.

A first reticulocyte measurement device embodying features of the present invention includes: a flow cell for receiving a measurement sample that contains a reticulocyte measurement reagent and a whole blood sample; a light source for irradiating cells in the measurement sample with an excitation light; a first detector for detecting intensity of scattering light emitted from the cells irradiated with the excitation light; a second detector for detecting intensity of fluorescent light emitted from the cells irradiated with the excitation light; and an analysis unit for making a two-dimensional distribution diagram having two axes corresponding to scattering light intensity and fluorescent light intensity, for specifying a mature red blood cell region and a reticulocyte region in the two-dimensional distribution diagram, for dividing the reticulocyte region into a plurality of regions on the basis of the fluorescent light intensity, and for calculating a mean forward scattering light intensity and a mean fluorescent light intensity for each of the plurality of regions.

A second reticulocyte measurement device embodying features of the present invention includes: a flow cell for receiving a measurement sample that contains a reticulocyte measurement reagent and a whole blood sample; a light source for irradiating cells in the measurement sample with an excitation light; a first detector for detecting intensity of scattering light emitted from the cells irradiated with the excitation light; a second detector for detecting intensity of fluorescent light emitted from the cells irradiated with the excitation light; and an analysis unit for making a two-dimensional distribution diagram having two axes corresponding to scattering light intensity and fluorescent light intensity, for specifying a mature red blood cell region and a reticulocyte region in the two-dimensional distribution diagram, for calculating a mean forward scattering light intensity and a mean fluorescent light intensity for each of the mature red blood cell region and the reticulocyte region, and for calculating slope of a linear regression line representing a relationship between the mean forward scattering light intensity and the mean fluorescent light intensity.

A third reticulocyte measurement device embodying features of the present invention includes: a flow cell for receiving a measurement sample that contains a reticulocyte measurement reagent and a whole blood sample; a light source for irradiating cells in the measurement sample with an excitation light; a first detector for detecting intensity of scattering light emitted from the cells irradiated with the excitation light; a second detector for detecting intensity of fluorescent light emitted from the cells irradiated with the excitation light; and an analysis unit for making a two-dimensional distribution diagram having two axes corresponding to scattering light intensity and fluorescent light intensity, for specifying a mature red blood cell region and a reticulocyte region in the two-dimensional distribution diagram, for calculating a mean forward scattering light intensity in the mature red blood cell region and a mean forward scattering light intensity in the reticulocyte region, for plotting data on a graph having two axes corresponding to forward scattering light intensity in the mature red blood cell region and forward scattering light intensity in the reticulocyte region, and for calculating distance of the plotted data from a datum point predetermined on the graph.

DETAILED DESCRIPTION

The size of a reticulocyte (and red blood cell) is proposed to relate closely to the level of hemoglobin contained in its cell (see, for example: "New Red Cell Parameters on the Sysmex XE-2100 as Potential Markers of Functional Iron Deficiency" by C. Briggs, R. Rogers, B. Thompson, S. J. Machin in *Infus. Ther. Transfus Med*. 2001, 28, 256-262). Thus, to investigate the size of a reticulocyte is to investigate the hemoglobin level in the reticulocyte in an indirect manner, whereby allowing a hypochromic red blood cell whose hemoglobin level is reduced to be detected.

Iron deficiency anemia causes a reduction in the body iron level, which leads to a microcytic hypochromism. Since prior to treatment a red blood cell is small in size, a larger size reticulocyte newly produced as a result of treatment (e.g., with medication)—when compared with a mature red blood cell—reflects the production of a normal red blood cell. On the other hand, a red blood cell that is large in size prior to treatment (e.g., as in the case of a malignant anemia), a smaller sized reticulocyte newly produced as a result of treatment—when compared with a mature red blood cell—reflects the exertion of the therapeutic effect.

Figure 1:
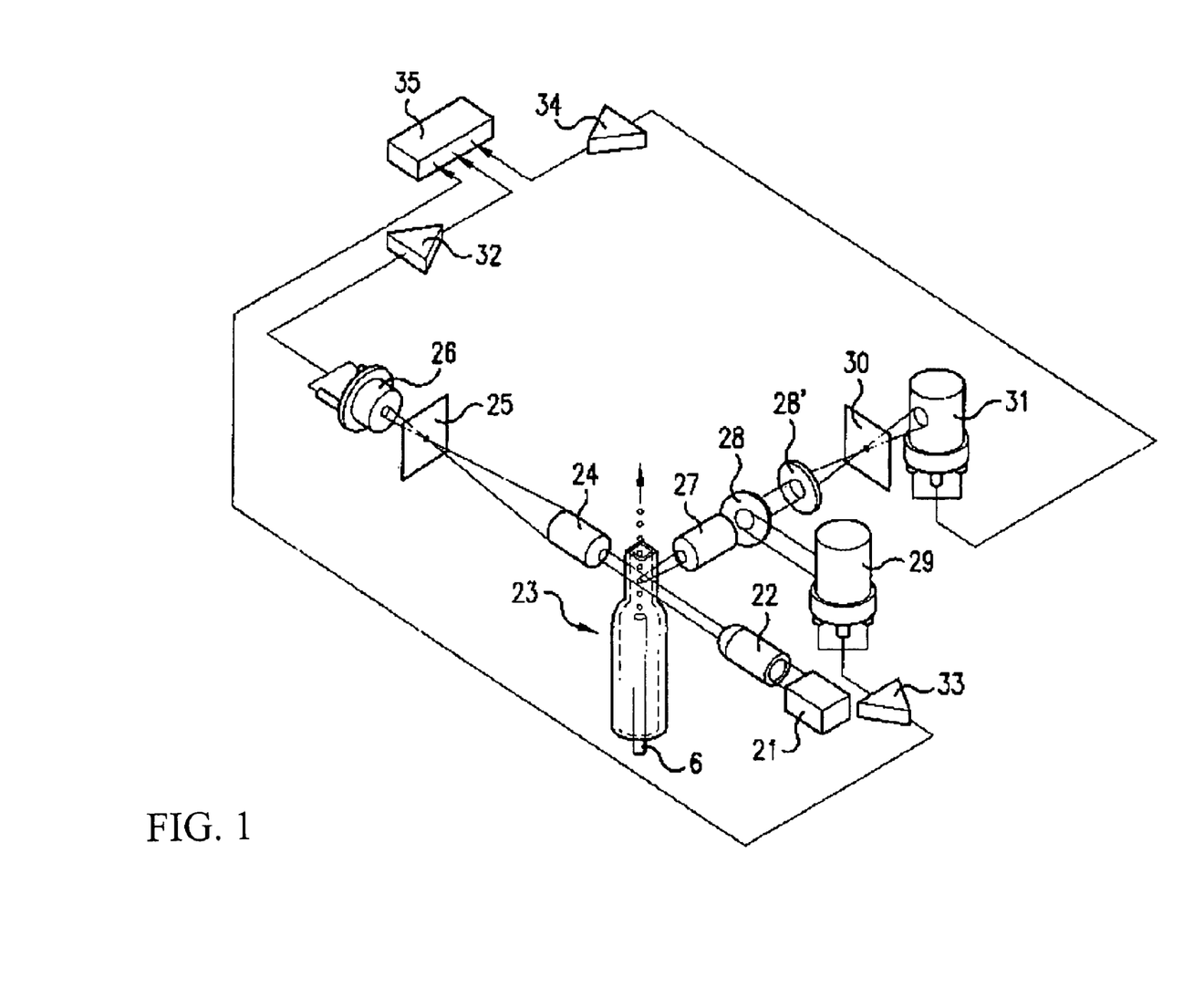
FIG. 1 shows a perspective view of a representative optical system for use in accordance with the present invention.

An example of an optical system of a flow cytometer in accordance with the present invention is shown in FIG. 1. In this figure, a beam emitted from an excitation light source (for example, a laser diode) 21 irradiates via a collimate lens 22 an orifice part of a sheath flow cell 23. Forward scattering light emitted from a blood cell ejected from a nozzle 6 and then passed through the orifice part comes via a condenser lens 24 and a pinhole plate 25 into a forward scattering light detector (photodiode) 26.

With regard to lateral scattering light and lateral fluorescent light emitted from a blood cell passing through the orifice part, the lateral scattering light comes via a condenser lens 27 and a dichroic mirror 28 into a lateral scattering light detector (photomultiplier tube) 29, while the lateral fluorescent light comes via the condenser lens 27, the dichroic mirror 28, a filter 29 and a pinhole plate 30 into a lateral fluorescent light detector (photomultiplier tube) 31.

A forward scattering light signal output from the forward scattering light detector 26, a lateral scattering light signal output from the lateral scattering light detector 29, and a lateral fluorescent light signal output from the lateral fluorescent light detector 31 are amplified by amplifiers 32, 33 and 34, respectively, and input into an analysis unit 35.

In this analysis unit 35, a two dimensional distribution (scattergram) is obtained using as parameters the lateral fluorescent light intensity and the forward scattering light intensity from the forward scattering signal and the lateral fluorescent light signal, respectively. The scattergram is then displayed in a display part (not shown), and the number of dots (or particles) within any region selected in the two dimensional distribution is counted and subjected to a desired arithmetic process. The counts and the arithmetic results are then displayed on the display part.

A reticulocyte measurement reagent employed in the invention may be any of the reagents known to those of ordinary skill in the art. For example, those described in the above-mentioned U.S. Pat. Nos. 4,544,546; 4,957,870; 5,360,739; and 5,821,127 may be employed.

The principles of measurement of a reticulocyte by flow cytometry are described below. First, RNA present in the reticulocyte is bound to a fluorescent dye to effect a staining, and then the stained reticulocyte is allowed to flow into a flow cell of a flow cytometer. The stained reticulocyte is irradiated with an excitation light. A scattering light and a fluorescent light thus emitted are then detected by a detector. The wavelength of the excitation light may be selected appropriately depending on the fluorescent dye employed.

A two dimensional distribution diagram (scattergram) whose two axes correspond to lateral fluorescent light intensity and forward scattering light intensity, respectively, is produced from a forward scattering signal and a lateral fluorescent light signal among the signals detected by the detector. A mature red blood cell region and a reticulocyte region are specified. Such a specification of these regions can be accomplished by methods, such as those described in U.S. Pat. Nos. 5,006,986 and 5,117,358, the entire contents of which are incorporated herein by reference, except that in the event of any inconsistent disclosure or definition from the present application, the disclosure or definition herein shall be deemed to prevail. Since a mature reticulocyte contains no RNA in its cell, the resultant fluorescence is extremely low. A reticulocyte, which contains RNA, exhibits a relatively intense fluorescence. Thus, a cell having fluorescence at a certain level or higher may be regarded as a reticulocyte. Moreover, since fluorescent light intensity varies depending on the amount of RNA contained in a cell, the maturity of the reticulocyte can be determined on the basis of the resultant fluorescent light intensity. A higher fluorescent light intensity reflects a cell containing a higher amount of RNA, which corresponds to a more juvenile reticulocyte. In the case of a multiparameter automated hematology analyzer, such as the Model XE-2100 produced by SYSMEX CORPORATION, a reticulocyte is divided depending on its fluorescent light intensity into any of the three regions of HFR (high fluorescence ratio), MFR (middle fluorescence ratio) and LFR (low fluorescence ratio). Most juvenile reticulocytes are located in the HFR region.

Upon measuring a reticulocyte, a method embodying features of the present invention focuses also on the size of a cell in contrast to conventional methods that focus only on the fluorescent light intensity (i.e., RNA quantity). Since a forward scattering light intensity obtained by measuring a reticulocyte by flow cytometry reflects the size of the cell, it may be employed as information for the cell size. For example, a mature red blood cell region and a reticulocyte region are specified on the two dimensional distribution diagram (scattergram). The ordinate of the diagram corresponds to forward scattering light intensity and the abscissa of the diagram corresponds to lateral fluorescent light intensity. The specified reticulocyte region is subjected to determination of the mean forward scattering light intensity. After a patient is treated with a therapeutic agent, the reticulocyte in the blood of the patient is measured, and the change in the measured value is monitored at after certain time interval, thereby monitoring the therapeutic effect. In addition, the regions classified based on the maturity of the reticulocyte (HFR, MFR, LFR described above) are also subjected to a determination of mean forward scattering light intensities in the respective regions, thereby obtaining additional detail regarding the therapeutic effect.

It is also possible to evaluate the therapeutic effect by dividing a reticulocyte region into a plurality of regions (i.e., at least 2 and preferably 3 regions) based on the fluorescent light intensity, calculating the mean forward scattering light intensity and the mean fluorescent light intensity in the respective divided regions, obtaining from these calculated values a linear regression line that represents the relationship between mean forward scattering light intensity and mean fluorescent light intensity, calculating the slope of the linear regression line, and detecting the change in the slope. The linear regression line may be obtained by a calculation that includes the values of the mean forward scattering light intensity and the mean fluorescent light intensity in the mature red blood cell region. Typically, each of the mature red blood cell, HFR, MFR and LFR regions is subjected to a calculation of the means of forward scattering light intensity and fluorescent light intensity. Then, a graph is produced employing the forward scattering light intensity as an ordinate and the fluorescent light intensity as an abscissa, and the mean values of the respective regions are plotted. By use of a least-squares method, an approximate line (linear regression line) of the respective plots may be obtained, and the change in its slope may be detected at a certain time interval, thereby judging the therapeutic effect. The slope of the linear regression line may be calculated from the mean forward scattering light intensity and the mean fluorescent light intensity of the mature red blood cell and the mean forward scattering light intensity and the mean fluorescent light intensity of the reticulocyte.

Figure 2:
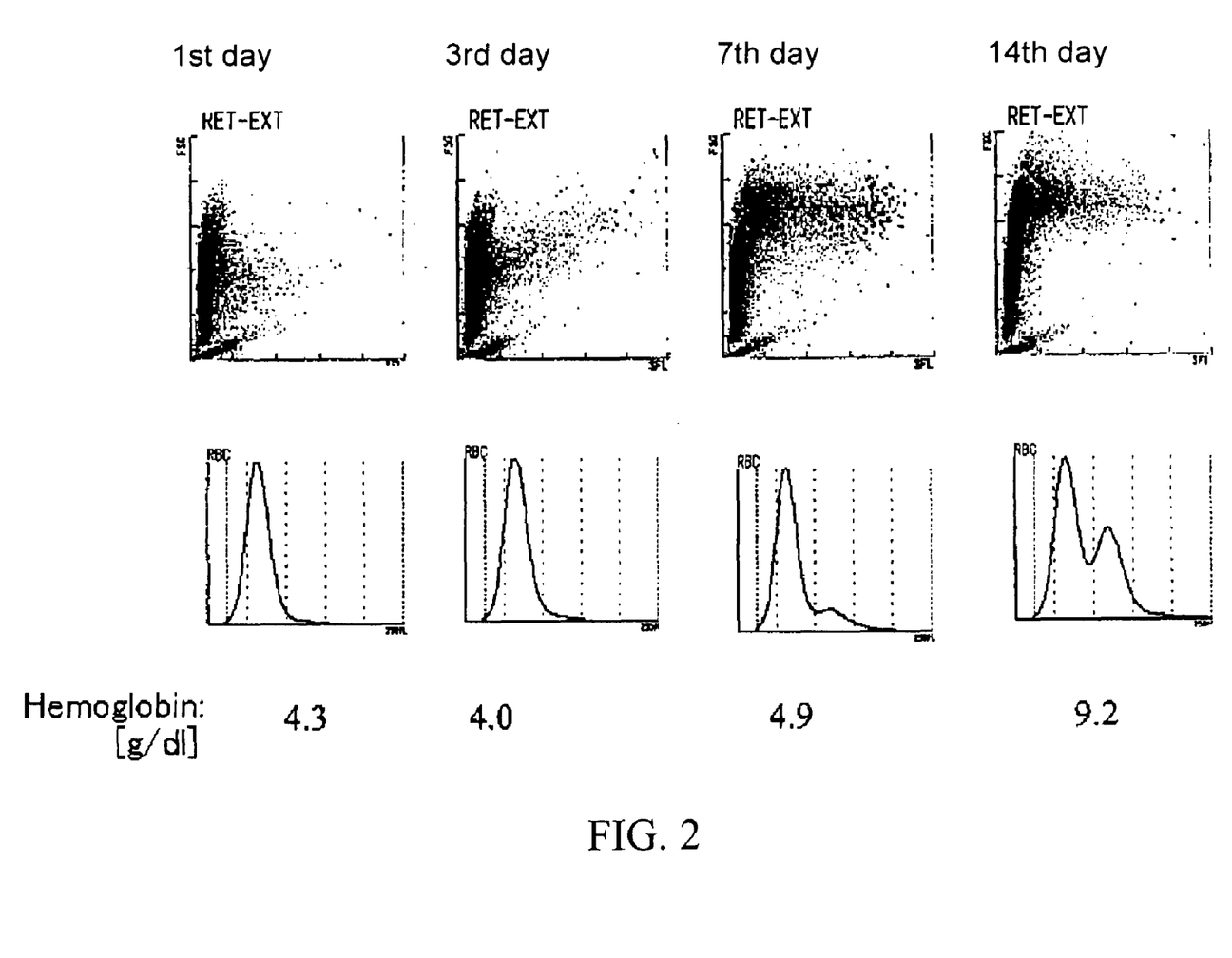
FIG. 2 shows the results of the measurement in Example 1 described below.

Alternatively, a graph having axes corresponding to the mean forward scattering light intensity of a reticulocyte and the mean forward scattering light intensity of a mature red blood cell may be produced and the measured data plotted on this graph, thereby obtaining a patient measurement point. A datum point is predetermined on this graph, and the distance between the disease patient measurement point and the datum point is calculated. This distance becomes shorter when the disease conditions improve, since the datum point becomes displayed as results. The peripheral blood measurement data on the 1st, 3rd, 7th and 14th day after the initiation of the therapy (i.e., medication) are obtained. These measurement data are introduced into a personal computer, where the analytical processing discussed below is performed. FIG. 2 shows the reticulocyte measurement scattergram, RBC histogram, and hemoglobin level.

Figure 3:
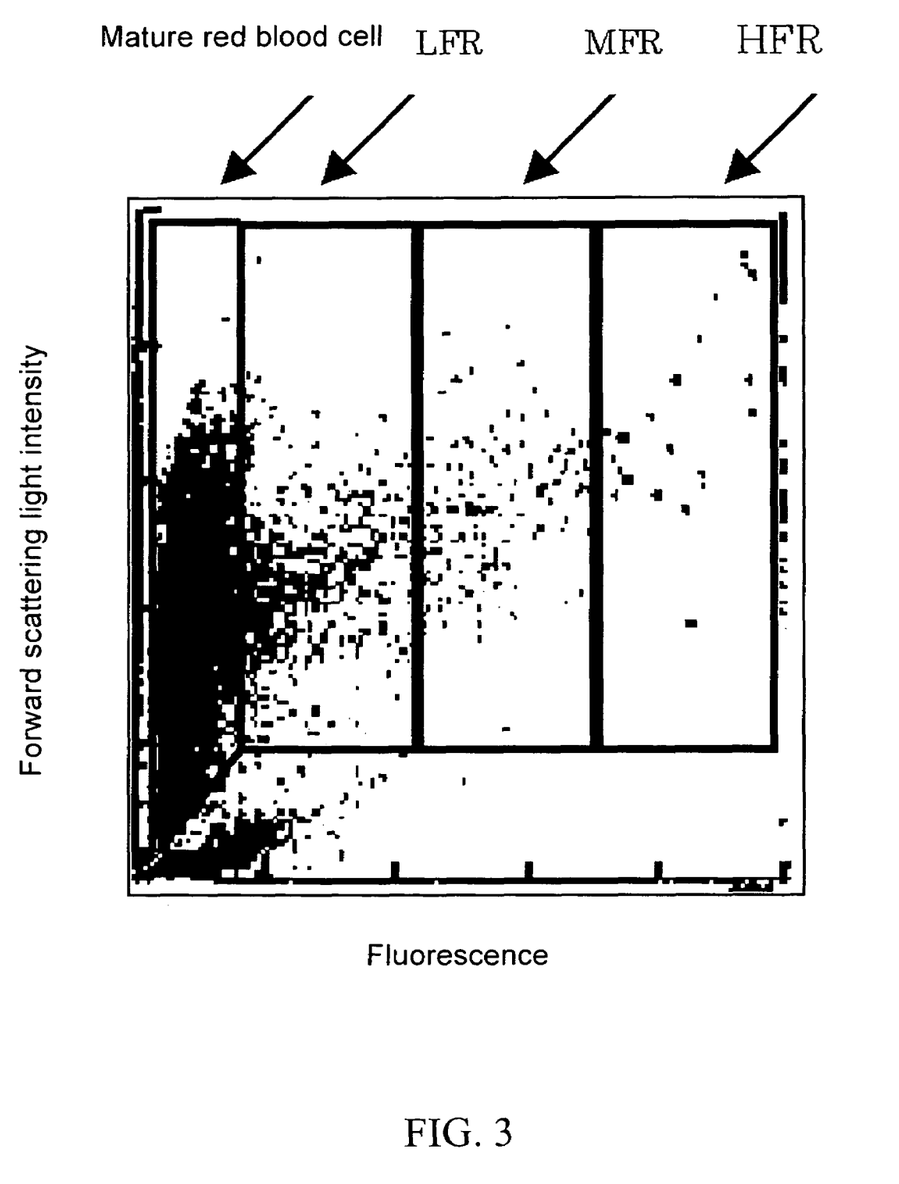
FIG. 3 shows a reticulocyte measurement scattergram in which the regions of the mature red blood cell, LFR, MFR and HFR are assigned.

On the scattergram, the areas of the mature red blood cell, LFR, MFR and HFR are assigned in order of lowest fluorescent intensities. A typical example is shown in FIG. 3. The mean forward scattering light intensity [ch.] and the mean fluorescent light intensity [ch.] of each area are obtained. The data obtained are plotted on the graph with an ordinate corresponding to forward scattering light intensity and an abscissa corresponding to lateral fluorescent light intensity. The approximate line of the respective plots is obtained by a least-squares method, and its slope is determined.

TABLE 1

| Day of measurement | RBC region | | LFR region | | MFR region | | HFR region | | |
| --- | --- | --- | --- | --- | --- | --- | --- | --- | --- |
| | Forward Scattering Light | Fluorescence | Forward Scattering Light | Fluorescence | Forward Scattering Light | Fluorescence | Forward Scattering Light | Fluorescence | Slope |
| 1 | 97 | 19 | 95 | 65 | 93 | 140 | 102 | 220 | 0.02 |
| 3 | 99 | 18 | 101 | 65 | 123 | 132 | 157 | 201 | 0.33 |
| 7 | 111 | 19 | 162 | 64 | 174 | 135 | 179 | 203 | 0.31 |
| 14 | 141 | 20 | 171 | 64 | 168 | 136 | 162 | 202 | 0.08 | closer. A point more remote to the datum point indicates a more marked condition of the disease. Accordingly, by detecting the change in this distance at a certain time interval, the therapeutic effect may be judged, as shown by the diagram in FIG. 5.

EXAMPLES

The following examples and representative procedures illustrate features in accordance with the present invention, and are provided solely by way of illustration. They are not intended to limit the scope of the appended claims or their equivalents.

Example 1

Monitoring Therapeutic Effect on Iron Deficiency Anemia

Peripheral blood of a patient having an iron deficiency anemia is measured by a full-automatic blood analyzing device Model XE-2100 (SYSMEX CORPORATION). In the XE-2100, RETSEARCH (II) (SYSMEX CORPORATION) is employed as a reticulocyte measurement reagent. 4.5 μl of the blood is diluted with 0.8955 ml of RETSEARCH (II) diluting solution and then combined with 18 μl of RETSEARCH (II) staining solution, and reacted for 31 seconds. From the sample thus prepared, a 2.8 μl aliquot is introduced into a flow cell and measured, thereby obtaining a reticulocyte scattergram represented as an analysis result. At the same time, a red blood cell histogram and hemoglobin amount measured by an electric resistance mode are also obtained and As shown above in the case of iron deficiency anemia, forward scattering light intensities increased in the order of LFR, MFR, HFR on the 3rd and 7th days after the initiation of treatment, and also exhibited an increased slope of the graph obtained by plotting scattering light intensity and fluorescent light intensity on the 3rd day. Such a change became evident at an earlier stage than in the RBC histogram. Accordingly, the fact that the newly produced reticulocyte underwent a change from a microcyte to a normocyte and had a normal function can be confirmed rather sooner and more correctly.

Example 2

Monitoring of Therapeutic Effect on Malignant Anemia

Figure 4:
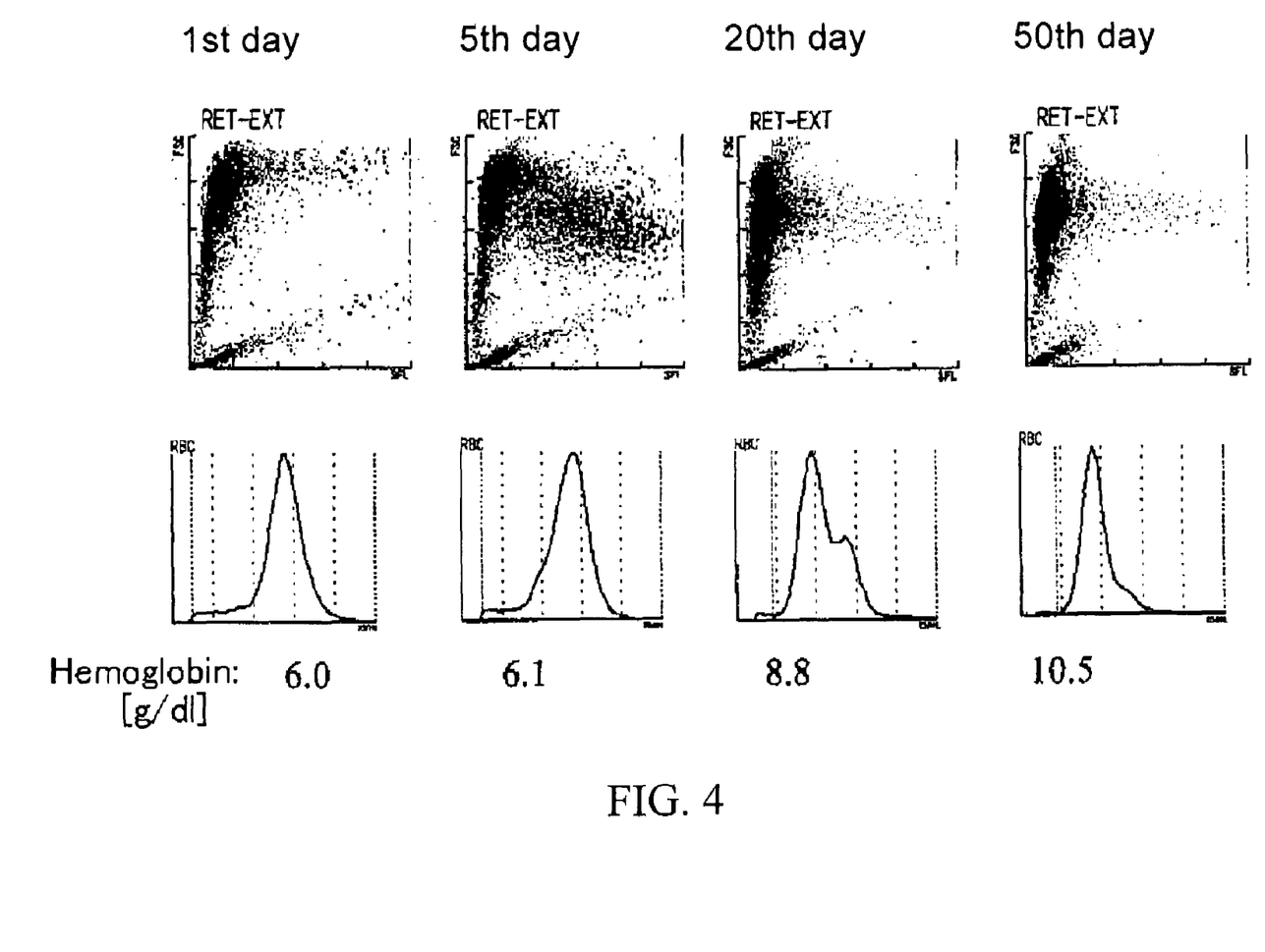
FIG. 4 shows the results of the measurement in Example 2 described below.

Peripheral blood of a patient having a malignant anemia is measured by an automated hematology analyzer Model XE-2100 (SYSMEX CORPORATION). A reticulocyte scattergram represented as an analysis result is obtained. At the same time, a red blood cell histogram and hemoglobin amount measured by an electric resistance mode are also obtained and displayed as results. The peripheral blood measurement data on the 1st, 5th, 20th and 50th day after the initiation of the therapy (i.e., medication) are obtained. These measurement data are introduced into a personal computer, where the analytical processing discussed below is performed. FIG. 4 shows the reticulocyte measurement scattergram, RBC histogram and hemoglobin level.

On the scattergram, the areas of the mature red blood cell, LFR, MFR and HFR are assigned in order of lowest fluorescent intensities. The mean forward scattering light intensity

[ch.] and the mean fluorescent light intensity [ch.] of each area are obtained. A graph with an ordinate corresponding to forward scattering light intensity and an abscissa corresponding to lateral fluorescent light intensity is produced. The approximate line of the respective plots is obtained by a least square method, and its slope is obtained.

TABLE 2

| Day of measurement | RBC region | | LFR region | | MFR region | | HFR region | | |
|---|---|---|---|---|---|---|---|---|---|
| | Forward Scattering Light | Fluorescence | Forward Scattering Light | Fluorescence | Forward Scattering Light | Fluorescence | Forward Scattering Light | Fluorescence | Slope |
| 1 | 195 | 27 | 211 | 79 | 215 | 145 | 216 | 218 | 0.10 |
| 5 | 197 | 27 | 177 | 78 | 156 | 144 | 148 | 215 | −0.26 |
| 20 | 174 | 25 | 178 | 79 | 165 | 144 | 151 | 216 | −0.13 |
| 50 | 167 | 26 | 170 | 79 | 168 | 143 | 169 | 217 | 0.01 |

As shown above in the case of malignant anemia, a negative slope of the graph was obtained by plotting scattering light intensity and fluorescent light intensity on the 5th day after the initiation of treatment. Such a change became evident at an earlier stage than in the RBC histogram. Accordingly, the fact that the newly produced reticulocyte underwent a change from a microcyte to a normocyte and had a normal function can be confirmed rather sooner and more correctly.

Example 3

Monitoring of Therapeutic Effect on Iron Deficiency Anemia 2

Figure 5:
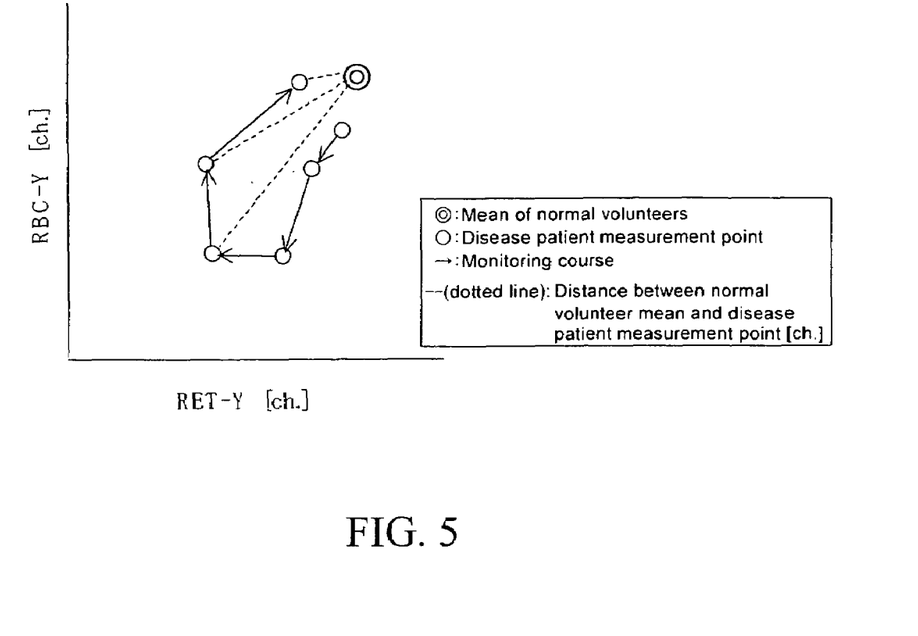
FIG. 5 shows a diagram of the monitoring in Example 3 described below.

Peripheral blood of a patient having an iron deficiency anemia is measured by an automated hematology analyzer Model XE-2100 (SYSMEX CORPORATION). A reticulocyte scattergram represented as an analysis result is obtained. The abscissa of the scattergram represents fluorescent light intensity, while the ordinate represents forward scattering light intensity. These measurement data are introduced into a personal computer, where the analytical processing discussed below is performed. On the scattergram, the mature red blood cell region is assigned, and the mean forward scattering light intensity (hereinafter abbreviated as RBC-Y) in the region is determined. Similarly, the reticulocyte region is assigned on the scattergram, and the mean forward scattering light intensity (hereinafter abbreviated as RET-Y) in the region is determined. Then, a graph having an abscissa corresponding to RBC-Y and an ordinate corresponding to RET-Y is produced. The measurement data are plotted on this graph, thereby obtaining a patient measurement point. Initially, the mean values of the RBC-Y and RET-Y data in normal volunteers (133 cases) are calculated, and plotted on this graph, thereby obtaining a normal volunteer mean point (datum point). Then, the distance from the datum point to the disease patient measurement point is determined. FIG. 5 shows a diagram for obtaining the distance. When the coordinate of the datum point is assigned to (RET-Ys, RBC-Ys) and the coordinate of the disease patient measurement point is assigned to (RET-Yn, RBC-Yn) in FIG. 5, then the distance between the two points can be calculated in accordance with the following equation:

$$D=\sqrt{(RET\text{-}Ys-RET\text{-}Yn)^2+(RBC\text{-}Ys-RBC\text{-}Yn)^2}$$

Figure 6:
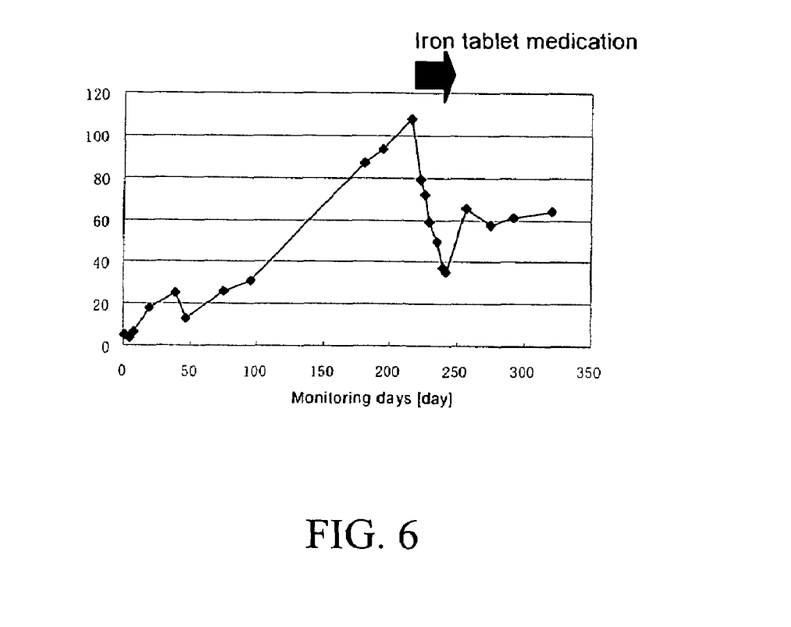
FIG. 6 shows the results of the monitoring in Example 3 described below.
Figure 7:
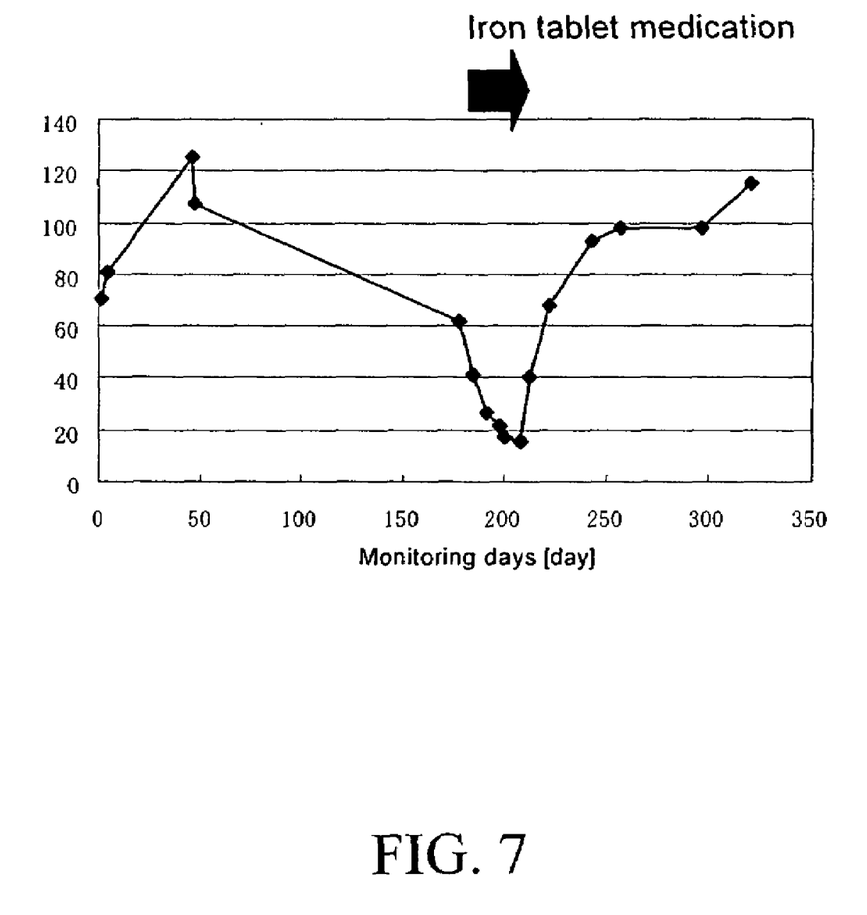
FIG. 7 shows another example of the results of the monitoring in Example 3 described below.

The distance becomes shorter when the conditions of the iron deficiency anemia patient improve since the datum point becomes closer. A point more remote to the datum point gives smaller RBC-Y and RET-Y, which correspond to a more marked condition of the iron deficiency. Accordingly, by monitoring this distance, the anemic conditions of the patient can be known. FIG. 6 represents a typical example. After initiating the monitoring, the conditions became advanced, and the iron tablet formulation medication around the 215th day resulted in an improvement of conditions. A similar example is shown in FIG. 7. While the iron tablet formulation given on the 178th day after the initiation of treatment resulted in an improvement of conditions, an exacerbation was noted again on the 207th day and later.

As is abundantly clear from the description above, the present invention allows the therapeutic effect in a red blood cell-related disease to be known at an earlier stage and rather objectively.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:
1. A method for measuring a reticulocyte comprising:
(a) preparing a measurement sample by mixing a reticulocyte measurement reagent and a whole blood sample from a subject;
(b) introducing the measurement sample into a flow cell of a flow cytometer;
(c) irradiating cells in the measurement sample flowing in the flow cell with an excitation light;
(d) detecting scattering light and fluorescent light emitted from the cells;
(e) making a two-dimensional distribution diagram having two axes corresponding to forward scattering light intensity and fluorescent light intensity, respectively;
(f) specifying a mature red blood cell region and a reticulocyte region in the two-dimensional distribution diagram;
(g) calculating a first mean forward scattering light intensity in the reticulocyte region;
(h) calculating a second mean forward scattering light intensity by performing (a) through (g) using a whole blood sample taken from the subject after a period of time and after administration of a therapeutic agent for anemia to the subject;
(i) detecting a difference between the first and the second mean forward scattering light intensities; and
(j) outputting monitoring information of a therapeutic effect of the agent on anemia based on the difference.

2. The method of claim 1 further comprising:
dividing the reticulocyte region into a plurality of regions on the basis of the fluorescent light intensity; and
calculating the mean forward scattering light intensity of each of the plurality of regions.

3. A method for measuring a reticulocyte comprising:
(a) preparing a measurement sample by mixing a reticulocyte measurement reagent and a whole blood sample;
(b) introducing the measurement sample into a flow cell of a flow cytometer;
(c) irradiating cells in the measurement sample flowing in the flow cell with an excitation light;
(d) detecting scattering light and fluorescent light emitted from the cells;
(e) making a two-dimensional distribution diagram having two axes corresponding to forward scattering light intensity and fluorescent light intensity, respectively;
(f) specifying a mature red blood cell region and a reticulocyte region in the two-dimensional distribution diagram;
(g) dividing the reticulocyte region into a plurality of regions on the basis of the fluorescent light intensity; and
(h) calculating a mean forward scattering light intensity and a mean fluorescent light intensity for each of the plurality of regions.

4. The method of claim 3 further comprising calculating a slope of a linear regression line representing a relationship between the mean forward scattering light intensity and the mean fluorescent light intensity in the plurality of regions divided out.

5. The method of claim 4 wherein the slope of the linear regression line is calculated while including data of the mean forward scattering light intensity and the mean fluorescent light intensity in the mature red blood cell region.

6. A method for measuring a reticulocyte comprising:
(a) preparing a measurement sample comprising a reticulocyte measurement reagent and a first whole blood sample;
(b) introducing the measurement sample into a flow cell of a flow cytometer;
(c) irradiating cells in the measurement sample flowing in the flow cell with an excitation light;
(d) detecting scattering light and fluorescent light emitted from the cells;
(e) making a two-dimensional distribution diagram having two axes corresponding to forward scattering light intensity and fluorescent light intensity, respectively;
(f) specifying a mature red blood cell region and a reticulocyte region in the two-dimensional distribution diagram;
(g) calculating a mean forward scattering light intensity and a mean fluorescent light intensity in the mature red blood cell region and the reticulocyte region; and
(h) calculating a first slope of a first linear regression line representing a relationship between the mean forward scattering light intensity and the mean fluorescent light intensity in the mature red blood cell region and the reticulocyte region.

7. The method of claim 6 wherein the first whole blood sample is taken from a subject, and wherein the method further comprises:
determining a slope of a second linear regression line corresponding to a second whole blood sample taken from the subject after a period of time; and
detecting change in slope of the first and the second linear regression lines.

8. A method for measuring a reticulocyte comprising:
(a) preparing a measurement sample comprising a reticulocyte measurement reagent and a whole blood sample;
(b) introducing the measurement sample into a flow cell of a flow cytometer;
(c) irradiating cells in the measurement sample flowing in the flow cell with an excitation light;
(d) detecting scattering light and fluorescent light emitted from the cells;
(e) making a two-dimensional distribution diagram having two axes corresponding to forward scattering light intensity and fluorescent light intensity, respectively;
(f) specifying a mature red blood cell region and a reticulocyte region in the two-dimensional distribution diagram;
(g) calculating a mean forward scattering light intensity in the mature red blood cell region and a mean forward scattering light intensity in the reticulocyte region;
(h) plotting data obtained in (g) on a graph having two axes corresponding to the forward scattering light intensity in the mature red blood cell region and the forward scattering light intensity in the reticulocyte region, respectively; and
(i) calculating distance of the data plotted in (h) from a datum point predetermined on the graph.

9. A reticulocyte measurement device comprising:
a flow cell for receiving a measurement sample that comprises a reticulocyte measurement reagent and a whole blood sample;
a light source for irradiating cells in the measurement sample with an excitation light;
a first detector for detecting intensity of scattering light emitted from the cells irradiated with the excitation light;
a second detector for detecting intensity of fluorescent light emitted from the cells irradiated with the excitation light; and
an analysis unit for making a two-dimensional distribution diagram having two axes corresponding to scattering light intensity and fluorescent light intensity, for specifying a mature red blood cell region and a reticulocyte region in the two-dimensional distribution diagram, for dividing the reticulocyte region into a plurality of regions on the basis of the fluorescent light intensity, and for calculating a mean forward scattering light intensity and a mean fluorescent light intensity for each of the plurality of regions.

10. The device of claim 9 wherein the analysis unit further comprises means for calculating a slope of a linear regression line representing a relationship between the mean forward scattering light intensity and the mean fluorescent light intensity.

11. A reticulocyte measurement device comprising:
a flow cell for receiving a measurement sample that comprises a reticulocyte measurement reagent and a whole blood sample;
a light source for irradiating cells in the measurement sample with an excitation light;
a first detector for detecting intensity of scattering light emitted from the cells irradiated with the excitation light;
a second detector for detecting intensity of fluorescent light emitted from the cells irradiated with the excitation light; and
an analysis unit for making a two-dimensional distribution diagram having two axes corresponding to scattering light intensity and fluorescent light intensity, for specifying a mature red blood cell region and a reticulocyte region in the two-dimensional distribution diagram, for calculating a mean forward scattering light intensity and a mean fluorescent light intensity for each of the mature red blood cell region and the reticulocyte region, and for calculating slope of a linear regression line representing a relationship between the mean forward scattering light intensity and the mean fluorescent light intensity.

12. A reticulocyte measurement device comprising:

a flow cell for receiving a measurement sample that comprises a reticulocyte measurement reagent and a whole blood sample;

a light source for irradiating cells in the measurement sample with an excitation light;

a first detector for detecting intensity of scattering light emitted from the cells irradiated with the excitation light;

a second detector for detecting intensity of fluorescent light emitted from the cells irradiated with the excitation light; and an analysis unit for making a two-dimensional distribution diagram having two axes corresponding to scattering light intensity and fluorescent light intensity, for specifying a mature red blood cell region and a reticulocyte region in the two-dimensional distribution diagram, for calculating a mean forward scattering light intensity in the mature red blood cell region and a mean forward scattering light intensity in the reticulocyte region, for plotting data on a graph having two axes corresponding to forward scattering light intensity in the mature red blood cell region and forward scattering light intensity in the reticulocyte region, and for calculating distance of the plotted data from a datum point predetermined on the graph.

* * * * *